(12) United States Patent
Oxenrider

(10) Patent No.: US 9,222,130 B2
(45) Date of Patent: Dec. 29, 2015

(54) METHOD AND APPARATUS FOR SEQUENCING MOLECULES

(71) Applicant: Keith Oxenrider, Sliver Spring, MD (US)

(72) Inventor: Keith Oxenrider, Sliver Spring, MD (US)

( * ) Notice: Subject to any disclaimer, the term of this patent is extended or adjusted under 35 U.S.C. 154(b) by 113 days.

(21) Appl. No.: 13/841,499

(22) Filed: Mar. 15, 2013

(65) Prior Publication Data

US 2014/0273186 A1   Sep. 18, 2014

(51) Int. Cl.
| | | |
|---|---|---|
| C12M 1/34 | (2006.01) | |
| C12M 3/00 | (2006.01) | |
| C12Q 1/68 | (2006.01) | |
| C12P 19/34 | (2006.01) | |
| G01N 15/06 | (2006.01) | |
| G01N 33/00 | (2006.01) | |
| G01N 33/48 | (2006.01) | |
| C07H 21/02 | (2006.01) | |
| C07H 21/04 | (2006.01) | |

(52) U.S. Cl.
CPC .................................. C12Q 1/6869 (2013.01)

(58) Field of Classification Search
USPC ........... 435/6.1, 6.11, 7.1, 91.1, 283.1, 287.1, 435/287.2; 436/94, 501; 536/23.1, 24.3, 536/24.33; 530/300, 350; 422/50, 68.1; 977/704, 705, 706, 713, 714, 717, 720, 977/721, 728, 730, 756, 789, 792, 793, 902, 977/924
See application file for complete search history.

(56) References Cited

U.S. PATENT DOCUMENTS

| | | | |
|---|---|---|---|
| 5,846,708 A | 12/1998 | Hollis et al. | |
| 2005/0186576 A1 | 8/2005 | Chan et al. | |
| 2005/0255581 A1* | 11/2005 | Kim et al. | 435/287.2 |
| 2007/0190543 A1* | 8/2007 | Livak | 435/6 |
| 2008/0254995 A1 | 10/2008 | Kim et al. | |
| 2010/0289505 A1 | 11/2010 | Zhang | |
| 2010/0331194 A1 | 12/2010 | Turner et al. | |
| 2012/0021408 A1 | 1/2012 | Ju et al. | |
| 2012/0282709 A1 | 11/2012 | Lee et al. | |
| 2012/0316075 A1 | 12/2012 | Buzby et al. | |
| 2013/0164541 A1* | 6/2013 | Suwa et al. | 428/412 |

OTHER PUBLICATIONS

Branton et al., The potential and challenges of nanopore sequencing. Nature Biotechnology, 26, 1146-1153, 2008.*
Vankatesan et al.,Nanopore sensors for nucleic acid analysis. Nature Nanotechnology, 6, 615-624, 2011.*

(Continued)

*Primary Examiner* — Frank Lu
(74) *Attorney, Agent, or Firm* — David Kulik; Williams Mullen PC

(57) ABSTRACT

The invention comprises a polymer sequencing chip. In one embodiment, an open nano channel is used in the surface of a semiconductor material or glass as a conduit for the polymer and the resulting monomers released from the polymer. As the resulting monomers pass through the nano channel, a detection device reads the sequence of monomers. Preferably, multiple micro LEDs are used to emit a signal when different monomer units pass through a region of the nano channel, such that multiply parallel sequencing operations can be conducted at the same time on a chip.

14 Claims, 4 Drawing Sheets

(56) References Cited

OTHER PUBLICATIONS

Astier et al., Toward Single Molecule DNA Sequencing: Direct Identification of Ribonucleoside and Deoxyribonucleoside 5'-Monophosphates by Using an Engineered Protein Nanopore Equipped with a Molecular Adapter. J. Am. Chem. Soc.,128, 1705-1710, 2006.*

International Search Report and Written Opinion mailed, Jul. 3, 2014, in related International Application No. PCT/us14/25291, filed Mar. 13, 2014.

* cited by examiner

METHOD AND APPARATUS FOR SEQUENCING MOLECULES

BACKGROUND OF THE INVENTION a. Field of the Invention

The invention relates to methods and devices that can be used to determine the structure of long chain molecules, with DNA sequences being the preferred type of molecule. DNA and other long chain biomolecules contain sequences of individual units that are present in a sequence that can be read from one end to the other. The devices and methods of the invention employ detecting elements to elucidate the sequence of individual units, and in the case of DNA the nucleic acid bases present. With many multiples of the detection elements being placed on a single chip, the devices of the invention provide an economical, efficient, and robust method for determining the base pair sequence of DNA, for example.

b. Background Art

Currently, methods to sequence biomolecules are relatively slow, inefficient, and require estimations or approximations to complete actual sequences for large collections, like those in the genome of an organism. Nanochip designs have generally taken the approach of using nanopore sensors, employing three dimensional pores into which the DNA molecule is supposed to travel in order to be sequenced. Venkatesan, Nature Nanotechnology 6:615 (2011); U.S. Pat. No. 8,105,846. These devices are necessarily limited by the ability to reliably direct molecules through the nanopore or other opening and are subject to "clogging" or other drawbacks that prevent useful operation.

As the skilled artisan appreciates, improved methods that can determine the actual sequence of a biomolecule and report that sequence info in real time or near to real time from a detection system provides significant advantages over existing techniques.

BRIEF SUMMARY OF THE INVENTION

The present invention provides a new method and apparatus for sequencing long chain polymers and biomolecules. Like the previously mentioned nanopore concepts, but unlike the conventional commercial sequencing approaches, the invention sequences at the single, unmodified molecule level. Unlike the nanopore approaches, however, the invention in one aspect avoids the necessity of directing a molecule into a pore or opening. Instead, the molecule flows down a "nano channel" on a chip that is open on at least one side or dimension. A simple example is a glass slide or semiconductor surface. The pore approaches are inherently three dimensional in that there is a flat plain (silicon in some and lipid bilayer in others) through which there is a pore spanning the membrane, and the molecule must pass from the 'top' of the membrane through the pore and to the 'bottom' of the membrane. The present invention is inherently two dimensional in that there is a flat plain with a small groove or nano channel, through which the molecule flows. As the molecule flows down the nano channel, it moves past a mechanism to sequentially release each monomer unit of the polymer (for example, a DNA exonuclease in the case of a DNA molecule) and then the released monomers flow through the channel past one or more sequential detectors. The apparatus and methods can also be used for epigenetic analyses, where the raw, unmodified genomic DNA can be compared to other samples where epigenetic changes may be present.

Characterization of the monomers may be done by the change in conductivity between one or more pairs of electrodes on either side of the nano channel or area surrounding the nano channel. Many detectors for differentiating the charge of each DNA monomer unit, for example, have already been described in the art and can be adapted for use here. Optionally, the detection of the monomers may be done by capacitive sensing (see, for example, U.S. Pat. No. 6,828,800). In the adaption for this invention, the channel is ideally narrow enough to only allow a single polymer to enter it, around 10 nanometers in the case of double stranded DNA (dsDNA). Each monomer may have a characteristic change in conductivity/capacity as it passes through the detector region, allowing for the use of digital signal processing to reliably distinguish between monomers. In addition, or in the event that the monomers lack sufficient conductivity-distinguishing characteristics under the circumstances used, the relative migration rate through the channel, being optionally lined with molecules to optimize a differential migration rate of the monomers, can be measured and then used to distinguish between monomers and determine their sequence.

In a commercial system there would be a large number (likely on the order of 10's or 100's of thousands) of individual sequencers operating in parallel. Each sequencer may only generate sequence data at the rate of 100 monomers per second and may only operate for 100's of thousands of monomers. However, operating in parallel the aggregate of the sequencer units is capable of producing enough information to, for example, reliably sequence the diploid human genome in an hour or less. Preferably, in order to move the sequence information generated from the detectors along the nano channel to a scale with that many parallel processing elements, either substantial processing in situ and serializing the data should occur, or the data can be transmitted in parallel via an analog process for off-chip decoding and processing. The use of in situ embedded signal processing hardware with caching/buffering logic to then serially write the information 'off chip' is feasible and understood in the art. Also, methods for transferring the information from the sequencers/monomer detectors to a device to serially write the sequence data is known in the art. Thus, in one embodiment, the devices of the invention can be used for gathering the sequence data as a raw, "noisy" signal, and then using computer-based methods to verify what each nucleotide is within the signal. In another embodiment, the chips can be constructed in multiple layers using through-silicon-via technology (see U.S. Pat. No. 7,683,459) to produce multiply parallel structures. However, in an embodiment where the sequencing chip is intended to be disposable, to minimize the cost, an alternative approach is to use a series of small light emitting diodes (micro LED) or similar emitting devices that proportionally emit light according to the information from or changes detected by the sequencer units. Each LED would operate in parallel and asynchronously and would be read by an image capture device positioned in close proximity to the sequencing chip. The image capture device operates at a high frame rate such that it can easily distinguish between the monomers flowing through the nano channel.

Other than preferably having a high level of flatness in its construction, the base material of the chip is largely dependent on the method of digitizing the analog data as the monomers pass the detector(s). The final surface of the chip should be insulating, such as $SiO_2$ (glass), but that surface only needs to be a few 10's of nanometers thick as the channel depth is approximately 3-5 nm. The size/width of the detectors is such that preferably no more than one monomer is present at one time. In preferred embodiments, the width of the nano channel is the minimum feasible with the technology available. The smallest nano channel allows only a single polymer molecule to flow through for processing. In one preferred embodiment, the nano channel is about 10 nanometers wide. The nano channel is optionally lined with molecules to constrain its width or to limit the number of polymers entering at one time, for example to limit to a single polymer molecule within the nano channel and between the detectors at one time. The optional lining can be with molecules selected to inhibit the migration of the released monomers in order to improve the differential flow of monomers or the detection of monomers. In the event that digital signal processing limitations suggest a higher degree of distinguishing characteristics between monomers, the optional lining can be used to optimize the differential flow.

In general, the flow of polymers and the released monomers through the nano channel is by capillary action, from one micro reservoir to another. In other embodiments, the motive force to drive the polymer and resultant monomers through the channel may optionally be a supplied current, much like electrophoresis, or it may be the bulk movement of the fluid containing the molecule and monomers, optionally via wicking the fluid at the destination end. The present invention also addresses the difficulty previously associated with reading the sequence of monomers liberated as nucleic acids as they pass through and are detected in the channel. The micro LED option can include the use of a semiconductor die to comprise a LED die, e.g., an inorganic LED die. Alternatively, the semiconductor die may comprise a laser and may comprise a semiconductor material comprising or consisting essentially of at least one of GaN, AlN, InN, or an alloy or mixture thereof; or a semiconductor material comprising or consisting essentially of at least one of silicon, GaAs, GaN, InAs, AlAs, InP, GaP, AlP, InSb, GaSb, AlSb, ZnO, or an alloy or mixture thereof. In addition, for example, the light emitting source can be of an organic type such as an OLED or a PLED, or of an inorganic type such as a micro LED, a quantum dot laser, a nanostructured metallic source, a carbon nanotube source, a metal or polymer nanowire source, or a field-emission source. Assuming that one desires to use micro LEDs of about 2 to about 10 microns and a 3 $\mu m \times 3$ $\mu m$ spacing for LED on the chip, each manufactured chip can contain approximately 200,000 separate micro LED emitters. Related to the micro LED example are ferro liquid display and liquid crystal on silicon technologies, available in the art. These technologies would replace the light emitting element with a mirrored or other change in a micro "pixel" that has a relatively fast refresh rate and could be easily detected by an opto-electric device.

An object of the present invention is to provide an apparatus, or more specifically a chip, for sequencing biomolecules by determining the sequence of monomers present in the chain of molecules comprising that biomolecule. The apparatus comprises a surface material having disposed on it an open nano channel of two sides and a bottom, where the gap between the two sides is large enough for the biomolecule to pass freely through, and optionally small enough to preclude more than two or more molecules from passing through at the same time. The nano channel has at least two ends. At least two microreservoirs, one at an end of the channel, are formed to allow a flow of solution from one end of the channel to the other. A biomolecule cleavage agent capable of cleaving the biomolecule to produce resulting monomers, is linked to one end of the channel. A monomer detection device is also positioned to detect the resulting monomers as they pass through the nano channel. The surface material of the apparatus or chip is a silicon or semiconductor material, but will generally be coated or have non-conducting materials on the final surface. The width between the two sides of the nano channel is approximately 10 nm or less in optimal circumstances, and the depth is approximately 3 to about 5 nm. The monomer detection device can, in one embodiment, calculate the time a monomer flows from the one location across the nano channel to as second location across the nano channel. That time is compared to the average time a known monomer unit travels a similar distance of similar nano channel composition, and thus the detector assigns a monomer identity to the monomer flowing through the nano channel. A sequence of resulting monomers are identified and used to re-create the sequence of monomers in the original biomolecule. Other polymers, beyond biomolecules, can be sequenced in a similar manner.

One of the various monomer detection devices possible can also be an electrical conductivity recorder capable of detecting the resulting monomers and distinguishing one monomer unit from the other monomer units. The apparatus can further include a recording device for compiling the presence of monomers as the resulting monomers pass through the channel.

In a preferred embodiment, the chips or apparatus of the invention use a monomer detection device that comprises multiple micro LEDs, each micro LED arranged and connected to a detection device across the nano channel and capable of emitting a different signal for each of the possible resulting monomers. In conjunction with the micro LEDs, the apparatus uses an opto-electric reader to detect the different signals from a micro LED or other detectable change in the sequencer signal.

In another aspect, the invention includes a DNA sequencing apparatus. A solid-state surface is used with an open nano channel cut into the top of the surface. The channel is approximately 10 nm in width or less and has a first and second end. A set of microreservoirs in the surface of the apparatus are capable of holding a solution of the DNA and causing the DNA to flow into the first end of the channel toward a DNA cleavage agent linked to the first end of the channel and capable of cleaving the DNA into nucleotide monomer units. A detector positioned along the length of the nano channel can determine the presence of a nucleotide monomer. The detector can be an electrical conductivity recorder or a time-of-flow recorder. The flow of solution from the first end of the channel to the second end of the channel can be controlled in a number of ways, including capillary action, electrophoresis, removal of solution from one reservoir, or pumping. Multiple nucleotide monomer detectors can be positioned along the length of the nano channel. Also, the interior surfaces of the channel can at least partially be coated with a polymer material and the solid-state surface is capable of being covered with a lipid or oil composition. The apparatus further includes a nucleotide sequence recording device capable of compiling the identity of nucleotides cleaved from the DNA and passing through the nano channel. The nucleotide detection device can also comprise multiple micro LEDs, where each micro LED arranged and connected to a detection device across the nano channel and capable of emitting a different signal for each of the possible resulting nucleotides. As above, the apparatus can include an opto-electric reader to detect the different signals from a micro LED.

The apparatus of the invention can also be used for the sequencing of dsDNA molecules, where the molecule is separated into single strands. Separate cleavage regions for each of the strands of the dsDNA, comprising cleavage agents that will only cleave in one direction, and where separate nano channels conduct one, or substantially just one, of the single stranded DNA molecules can be designed. The sequence of each strand can then be used as a control or additionally parallel data set to construct a correct ds DNA sequence.

The foregoing and other aspects, features, details, utilities, and advantages of the present invention will be apparent from reading the following description and claims, and from reviewing the accompanying drawings.

DETAILED DESCRIPTION OF THE INVENTION

For purposes of illustration, the present invention will be described in connection with methods and systems for sequencing DNA in particular, but, as noted, other long chain polymers can be sequenced in a similar manner. For example, RNA, protein or enzyme biomolecules can be used in similar manner. Exemplary designs of the novel sequencing chips can include embedded circuitry that would collect and collate the generated information and then move it off-chip via a much smaller and fixed number of physical contacts. While that is feasible, doing so may employ substantial, embedded, on-chip hardware. Employing elements where the data is moved and processed off the chip, in parallel, in such a way that it minimizes the complexity of the sequencing chip, provides many advantageous results, including cost savings and robust, redundant data sets to construct a sequence. In one aspect, moving the data off in parallel employs light emitting diodes (LEDs) connected to each individual sequencer. The data would be read in parallel using a relatively ordinary CCD/CMOS image/video chip or opto-electronic device, as known in the art. The optimal characteristics of the capture chip are to be able to operate at high speed, on the order of 10's of kilohertz frame rates. Micro LEDs for the present use can be of the smallest size available. Optionally, a 2 micron by 3 micron micro LED can be used for high resolution signals.

Figure 1:
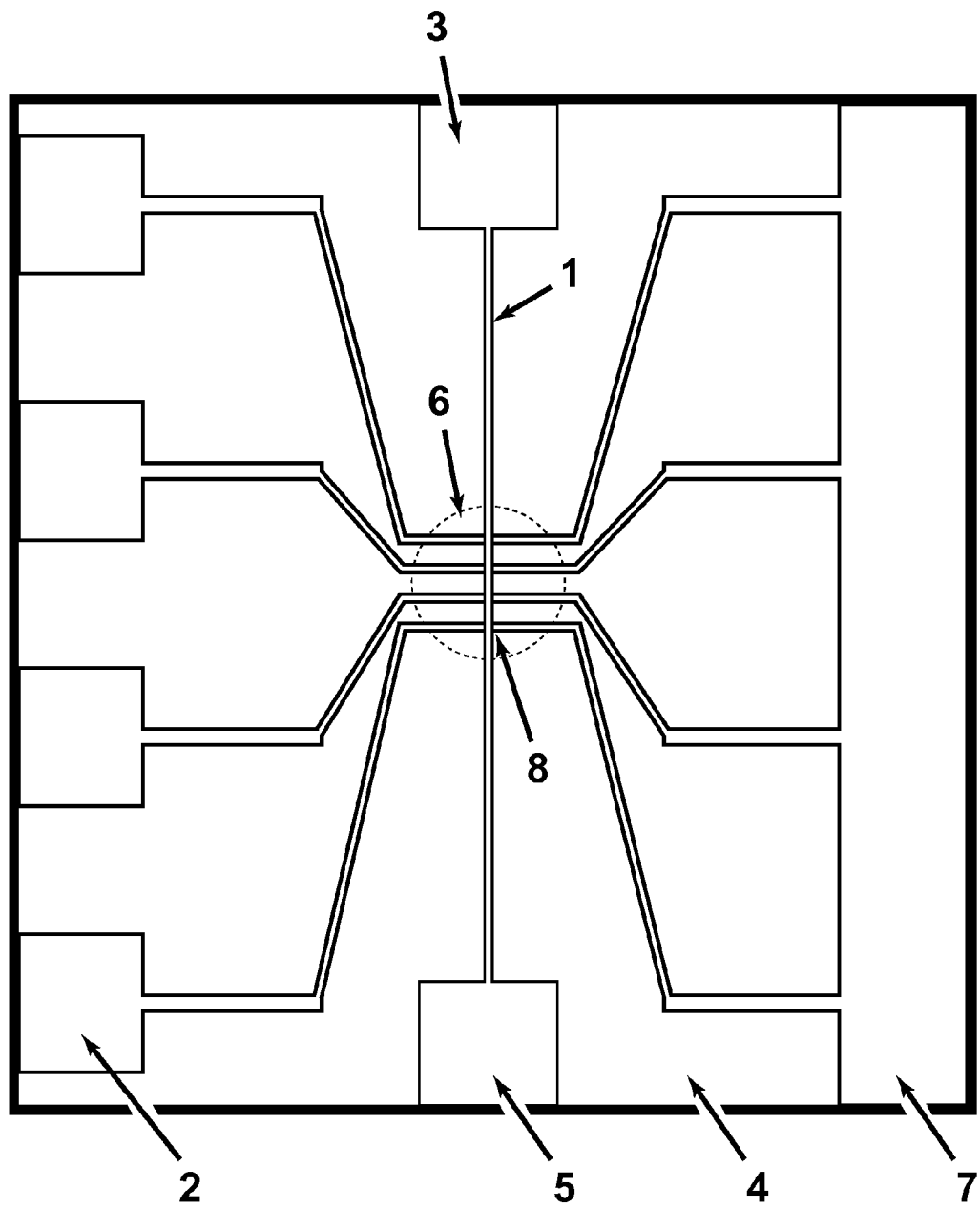
FIG. 1 is a schematic showing the exemplary surface of a chip (i.e., slide or semiconductor flat surface) from the top view. The chip surface material (4) contains a nano channel (1) from the top micro reservoir (3) to the bottom (5). The terms "top" and "bottom" here are used only to show a relationship as depicted in this schematic view and are not meant to limit the possible structures or orientations of any element on the surface of the chip. Area (6) contains along the nano channel contains multiple sequencers or detector devices for detecting the presence of a monomer units as it traverses the nano channel from (3) to (5) in this case. Each sequencer unit (2) on the left side can emit a signal or record the presence of a monomer as it passes the area in (6) where its connections cross the nano channel (8). In this example, a combined unit (7) operates with each of the separate units (2).
Figure 2A:
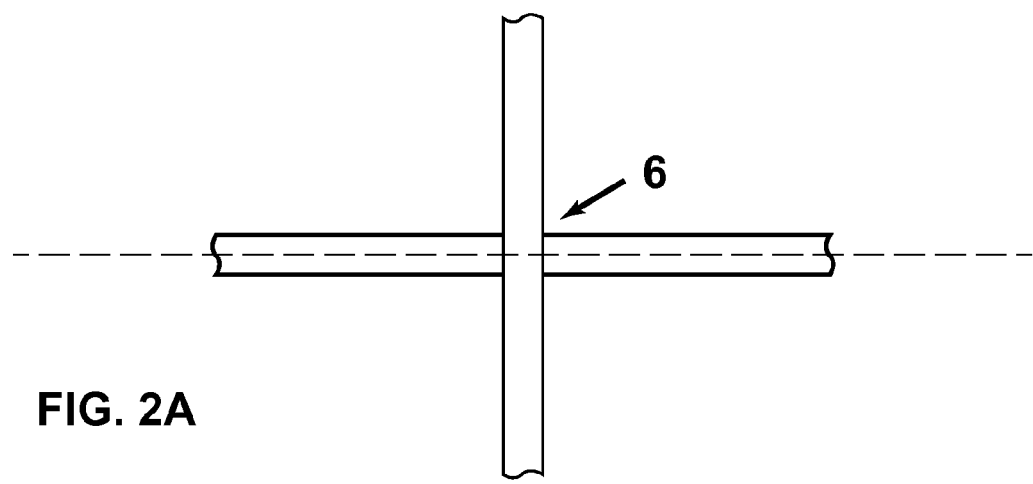
FIG. 2A is a close-up view of the schematic representation of the intersection between the nano channel and detector referred to in FIG. 1.
Figure 2B:
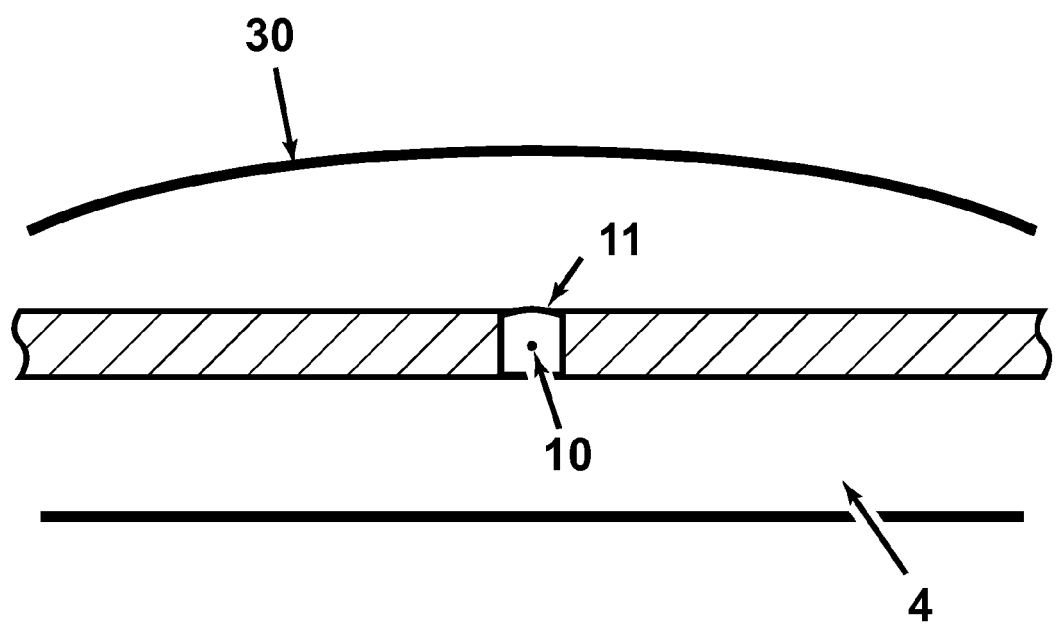
FIG. 2B is a schematic showing the molecule (10) to be sequenced within the open nano channel (11). The surface of the chip (4) can be covered with an oil or layer (30) to prevent evaporation of the solution containing the molecule.
Figure 3:
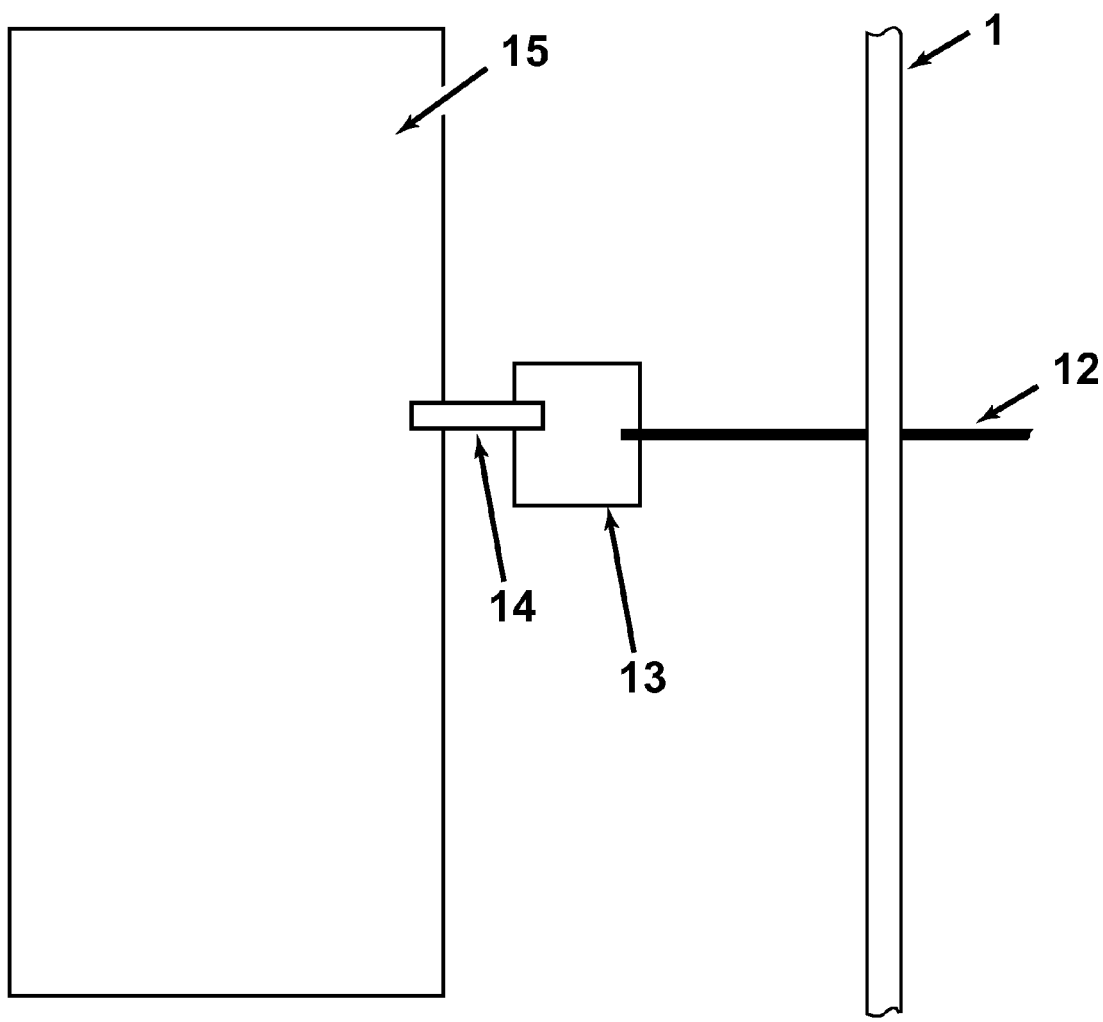
FIG. 3 schematically illustrates the exemplary arrangement of the detector elements. Nano channel (1) contains a region where detector parts cross the channel or are arranged on each side of the channel (12) to detect the presence of the monomers as they pass that location. The signal is relayed to optional processing element (13) and then relayed (14) to a signaling or recording element (15). In this schematic, the elements of the detector may or may not be present on a single chip.
Figure 4:
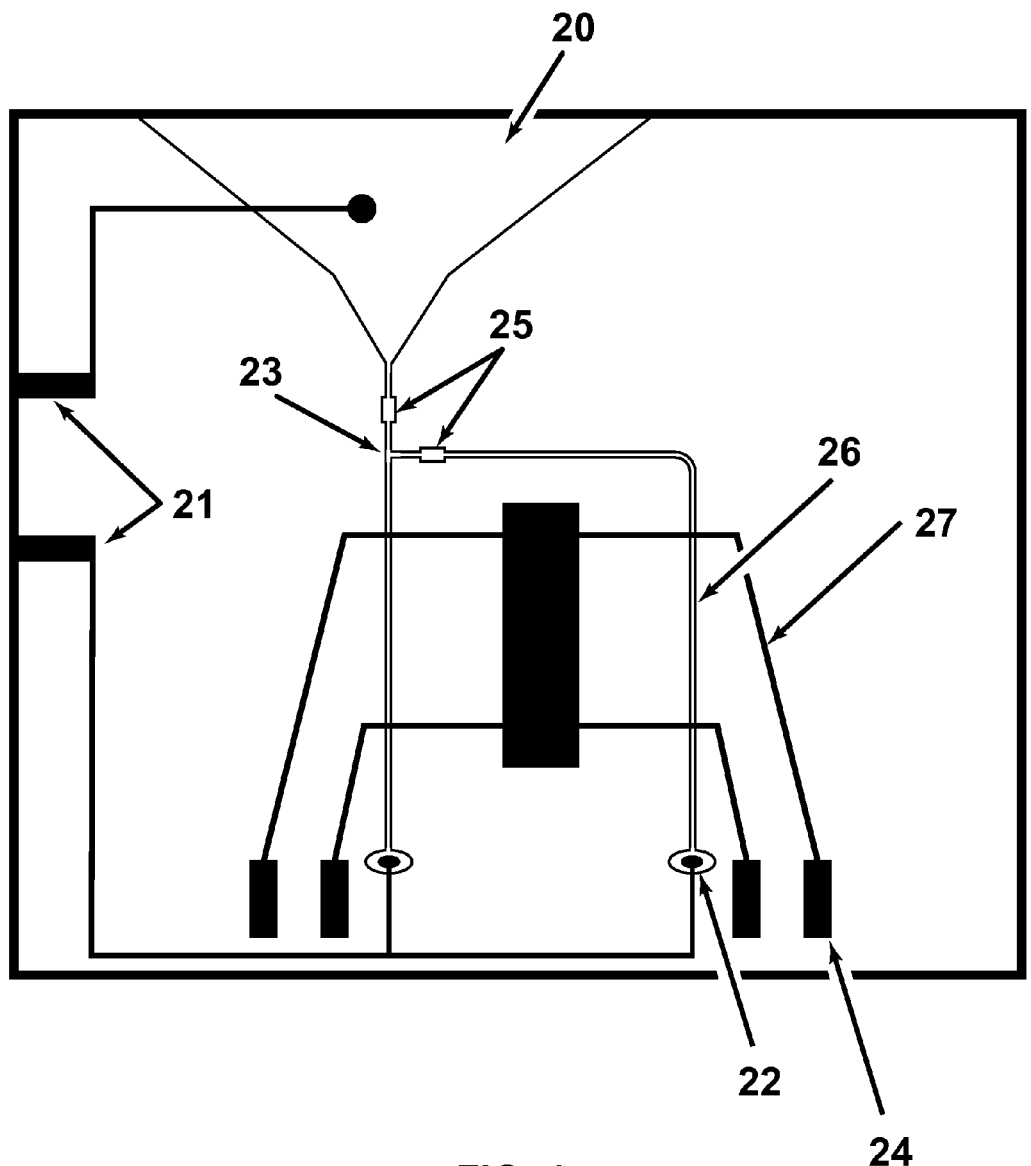
FIG. 4 schematically illustrates an alternative chip design. Reservoir (20) contains the polymer or molecule to be sequenced. Electric charge from (21) directs flow of molecule from reservoir (20) through nano channel (23), which here is split into two directions, to multiple final reservoirs (22). Regions (25) within channel can contain one or multiple cleavage agents, optionally cleaving with two or more different agents. Channel continues to sequencer regions (26) where sets of detectors (27) cross channel at various locations in order to detect presence of monomer as they pass that point along the channel.

In the schematic figures, the electrodes can all be connected to a common source and the LEDs and control circuitry can all be connected to a common source/ground. The nano channels are all connected to a common source or reservoir for the dsDNA, and all lead to a common (or possibly several shared, depending on layout constraints) reservoir sinks for the nucleotides. An amplifying transistor that is capable of using a faint signal from the electrode and boost it to the point where it can activate the LED can be incorporated into the design. One alternative to micro LEDs are the many options where one measures the voltage change as a single nucleotide moves through a region, or in the case of other examples a nanopore. This same measurement device can be adapted to the present chip. The nano channel of the invention, in one embodiment, is about 10 nanometers in width and about 3 to 5 nm in depth, as noted above. The electrode width may also be that narrow. The signal amplifier can be around 100 nm square (100 nm is a routine size in the integrated circuit fabrication capabilities) and the LED is, as mentioned above, around 2 microns by 3 microns. As shown in FIG. 4, separate paths of the nano channel are possible for separate molecules. Separating out the two strands of the dsDNA can thus employ two sets of sensors/detectors/LEDs. Preferably, the invention allows the sequencing of single strand DNA (ssDNA) molecules. In a preferred apparatus, a reusable holder or chip reader can be employed. The CCD camera receiver, or opto-electronic device to read the sequencer signals, and where software can do virtual alignment, will be present on the chip reader. As there are multiple parallel sequencers, it is not necessary for all the sequencers to work properly. Since they essentially operate independently of one another, if one has a defect or delay in signals for some reason it will not impact a neighboring sequencer.

The chips of the invention are intended to primarily provide a time-varying signal (optical in the case of the LED version, electronic in the case charge differential) that can be interpreted to reveal the sequence information. The software and/or hardware to interpret the signal and convert it to raw sequence data is described by several other micro sequencing apparatus available in the art.

Sequence reconstruction, in the circumstances of a reliable and reproducible interval between cleavage events to generate resulting monomer units, can employ detectors that are optimized for detecting a single base or nucleotide, so that the aggregation of information from parallel sequencers can recreate the original sequence. Alternatively, reconstruction with multiple parallel sequencers can use many recorded and repeated runs for each type of molecule and use the base/nucleotide, or monomer, with the highest fidelity as a correcting sample. If sequencing multiple copies of ssDNA using multiple detectors, each detector can read a different base in one example. One can then align the multiple, or in the case of DNA four sequences of monomers, to read on block of a repeated nucleotides. Once aligned, a final sequence representing the original sequence can be constructed.

In use, the apparatus of the invention can manage the secondary and tertiary structures in long DNA strands through the use of elevated temperatures on the chip or other denaturing conditions.

The present invention can also be used to provide a DNA sequence to detect at least one portion of a target DNA sequence in a molecule.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An apparatus for sequencing polymers by determining the sequence of monomers of the polymers in a chain of molecules, the apparatus comprising
    a surface material having an open nano channel consisting of two sides and a bottom, the gap between the two sides being large enough for a single molecule of the polymers to pass freely through but small enough to substantially prevent two or more molecules of the polymers of the same size from passing freely through, and the nano channel having two ends and being disposed on the surface;
    at least two microreservoirs, one at each end of the channel, the microreservoirs formed to allow a solution to flow from one end of the channel to the other end of the channel;
    a cleavage agent capable of cleaving the polymers to produce monomers, the cleavage agent linked to one end of the channel; and
    a monomer detection device positioned to detect the monomers as they pass through the channel wherein the monomer detection device is a device that calculates the time one of the monomers flows from one location of the nano channel to an another location of the nano channel; and
    a sequence reader device that records the signal from the monomer detection device.

2. The apparatus of claim 1, wherein the surface material is a silicon, semiconductor, or glass and the width between the two sides of the nano channel is approximately 10 nm or less and the depth approximately 3 to approximately 5 nm.

3. The apparatus of claim 1, wherein the monomer detection device comprises multiple micro light emitting diodes (LEDS), each of the multiple micro LEDS arranged and connected to a detection device of the nano channel and capable of emitting a different signal for each of the monomers.

4. The apparatus of claim 3, wherein the sequence reader device is an opto-electric reader to detect the different signals from micro LEDS.

5. The apparatus of claim 1, wherein the monomer detection device further comprises an electrical conductivity recorder capable of detecting the monomers and distinguishing one of the monomers from the other of the monomers.

6. The apparatus of claim 1, wherein the interior surfaces of the open nano channel are at least partially coated with a polymer material.

7. A DNA sequencing apparatus comprising
    a solid-state surface with an open nano channel cut into the top of the surface, the channel approximately 10 nm in width or less and about 3-5 nm in depth, the channel having a first end and a second end;
    a set of microreservoirs in the surface, the microreservoirs capable of holding a solution of DNA and causing the DNA to flow into the first end of the channel;
    a DNA cleavage agent linked to the first end of the channel and capable of cleaving the DNA into nucleotide monomers;
    a nucleotide monomer detection device positioned to detect the nucleotide monomers as they pass through the channel, wherein the nucleotide monomer detection device is a device that calculates the time one of the nucleotide monomers flows from a first location of the nano channel to a second location of the nano channel; and
    a detector positioned along the length of the channel for determining the presence of the nucleotide monomers.

8. The apparatus of claim 7, wherein the flow of the solution of DNA from the first end of the channel to the second end of the channel is controlled by capillary action, electrophoresis or removal of the solution of DNA from one microreservoir of said microreservoirs.

9. The apparatus of claim 7, further comprising multiple nucleotide monomer detectors positioned along the length of the channel.

10. The apparatus of claim 7, wherein the interior surfaces of the channel are at least partially coated with a polymer material and the solid-state surface is capable of being covered with a lipid or oil composition.

11. The apparatus of claim 7, wherein the detector comprises a nucleotide sequence recording device capable of compiling the identity of nucleotides cleaved from the DNA, and wherein the sequence recording device is optionally separate from the DNA sequencing apparatus.

12. The apparatus of claim 7 wherein the DNA sequencing apparatus is designed to sequence double-stranded DNA (dsDNA) molecules and employs separate cleavage regions formed on the surface for each of the strands of the dsDNA.

13. The apparatus of claim 7, wherein the nucleotide monomer detection device comprises multiple micro light emitting diodes (LEDS), each of the multiple micro LEDS arranged and connected to a detection device of the nano channel and capable of emitting a different signal for each of the nucleotide monomers.

14. The apparatus of claim 13, further comprising an opto-electric reader to detect the different signals from the micro LEDS.

* * * * *